United States Patent
Fujita (10) Patent No.: US 6,868,195 B2
(45) Date of Patent: Mar. 15, 2005

(54) DEVICE FOR DETECTING THREE-DIMENSIONAL SHAPES OF ELONGATED FLEXIBLE BODY

(75) Inventor: Hiroshi Fujita, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 10/780,636

(22) Filed: Feb. 19, 2004

(65) Prior Publication Data

US 2004/0165810 A1 Aug. 26, 2004

(30) Foreign Application Priority Data

Feb. 20, 2003 (JP) ........................................ 2003-042949

(51) Int. Cl.[7] .................................................. G02B 6/00
(52) U.S. Cl. ........................................ 385/12; 356/73.1
(58) Field of Search ..................... 385/12, 37; 356/73.1

(56) References Cited

U.S. PATENT DOCUMENTS 5,671,307 A * 9/1997 Lauzon et al. ................. 385/37
6,307,988 B1 * 10/2001 Eggleton et al. .............. 385/37
6,625,355 B2 * 9/2003 Wakabayashi et al. ........ 385/37

\* cited by examiner

Primary Examiner—Phan T. H. Palmer
Assistant Examiner—Jennifer Doan
(74) Attorney, Agent, or Firm—Oblon, Spivak, McClelland, Maier & Neustadt, P.C.

(57) ABSTRACT

For detecting three-dimensional shapes of an elongated flexible body, a sensor cable to be placed in a passage or channel which is formed axially and coextensively within the elongated flexible body. The sensor cable has two pairs of fiber Bragg grating strands within a tubular carrier casing. A signal light beam containing Bragg wavelength bands is projected from a light source to input same to refractive index change portions in the fiber Bragg grating strands. Reflection diffraction light signals from the refractive index change portions are received by a signal processor to measure the degree of strain at each one of the respective refractive index change portions by comparing wavelengths of the reflection diffraction light signals with reference wavelength.

6 Claims, 9 Drawing Sheets

DEVICE FOR DETECTING THREE-DIMENSIONAL SHAPES OF ELONGATED FLEXIBLE BODY

BACKGROUND OF THE INVENTION

1. Field of the Art

This invention relates to a device for detecting three-dimensional (3D) shapes and conditions of an elongated flexible body, for example, 3D shapes and conditions of bends in an endoscopic flexible insertion tube which has been introduced into a body cavity of a patient.

2. Prior Art

For instance, in the case of an endoscope for examination of lower digestive ducts, its insertion tube needs to be inserted into through a complicate path of insertion which contains three-dimensional bends, more specifically, through the intestinum rectum, sigmoid colon, and lower, transverse and ascending colons. Besides, the path of insertion is not always maintained in stable conditions and can easily change into different conditions upon application of an external force. Therefore, as the insertion tube is inserted along a path of insertion, in some cases the fore leading end of the insertion tube is pushed against an intracavitary wall portion and stuck on that intracavitary wall portion failing to advance to farther target points. In this manner, great difficulties are often experienced in operating the insertion tube of an endoscope along a path of insertion, and the insertion of the endoscopic insertion tube can impose an extremely great burden on the part of the patient unless it is operated with meticulous skill.

In consideration of the foregoing situations, various attempts have thus far been made to the development of a device which can three-dimensionally grip the shape of an endoscopic flexible insertion tube which has been introduced into a body cavity. It has been known, for example, from Japanese Laid-Open Patent Application H5-91972, to employ a pair of fiber optics having obliquely cut end faces connected at a predetermined open angle relative to each other, detecting conditions of a bend in the insertion tube by calculating the open angle between the end faces of the two fiber optics.

Further, it has been known, for example, from Japanese Laid-Open Patent Application 2002-131009, to detect a three-dimensional shape of an endoscopic biopsy channel by the use of four sense coils each consisting of four single-core coils and capable of detecting a magnetic field in the same direction and on the same straight line. The four sense coils are located at four equidistant spatial positions on an orbit around a bed on which a patient lies, while, for example, 16 source coils which are adapted to produce different high frequency drive signals are provided on a probe to be introduced into a body cavity of the patient through a biopsy channel within an insertion tube of an endoscope. In this case, coordinates of spatial positions of the respective source coils are calculated on the basis of magnetic field data of the source coils to detect the three-dimensional shape of the endoscopic biopsy channel in which the probe has been inserted, that is to say, to detect the three-dimensional shape of the insertion tube of the endoscope.

In this connection, in a case where spliced fiber optics couples are used in the manner as in the firstly mentioned prior art Japanese Laid-Open Patent Application H5-91972, four fiber optics couples are required to detect the shape of a bent portion at a certain position of an endoscopic insertion tube, necessitating to locate four fiber optics couples at intervals along the length of the endoscopic insertion tube. Therefore, in order to enhance resolution over the distance in the longitudinal direction of the insertion tube, namely, in order to increase the detection points along the length of the insertion tube, it becomes necessary to provide an extremely large number of fiber optics couples at short intervals along the length of the endoscopic insertion tube. On the other hand, in the case of secondly mentioned prior art Japanese Laid-Open Patent Application 2002-131009, it is an essential requisite to provide a bed with sense coils for detection of a 3D shape of the endoscopic insertion tube, which requires to make adjustments of a patient's lying position relative to the sense coils in addition to complicate signal processing operations.

SUMMARY OF THE INVENTION

In view of the foregoing situations, it is an object of the present invention to provide a device which is simplified and compact in construction but capable of detecting three-dimensional shapes of an elongated flexible body like a flexible insertion tube of an endoscope without necessitating complicate signal processing.

In accordance with the present invention, in order to achieve the above-stated objective, there is provided a device for detecting three-dimensional shapes of an elongated flexible body, which comprises: a sensor cable adapted to be inserted into an axial coextensive passage within an elongated flexible body, the sensor cable having two pairs of fiber Bragg grating strands each having a plural number of refractive index change portions periodically in a predetermined pitch; a light source connectible to each one of the fiber Bragg grating strands to input a light beam containing a Bragg wavelength to the refractive index change portions; and a signal processor adapted to receive reflection diffraction light signals from the refractive index change portions of each fiber Bragg grating strand, and to detect a three-dimensional shape of the elongated flexible body by measuring strains of the refractive index change portions on the basis of shifts of the reflection diffraction light signals from a reference wavelength.

Fiber Bragg grating (hereinafter referred to as "FGB" for brevity) is an optical fiber device having refractive index change portions in a core portion. When a light beam of a specific wavelength is input to the optical fiber, reflection diffraction light is produced at each refractive index change portion. The light of the specific wavelength is called "Bragg wavelength." The wavelength of the reflection diffraction light change when the refractive index change portions are strained. The greater the straining, the greater becomes the shift in wavelength. It follows that wavelength of reflection diffraction light from the refractive index change portions changes when a strand of FBG is bent. That is to say, the angle of bend in the FBG strand can be detected on the basis of shifts in wavelength of reflection diffraction light signals from the respective refractive index change portions.

In a preferred form of the present invention, a sensor cable is constituted by two pairs of FBG strands each having a plural number of refractive index change portions formed in a core portion periodically in a predetermined pitch. In this instance, the sensor cable is used by placing same in an axial passage which is formed coextensively through an elongated flexible body. Let alone flexibility, the sectional shape of the sensor cable depends on the sectional shape of the passage in which it is to be placed. In case the passage is non-circular in shape, e.g, square or oval, it is desirable to form the sensor cable in a corresponding shape. For instance, the sectional shape is circular in the case of a biopsy channel which is provided within a flexible insertion tube of an endoscope, so that the pairs of FBG strands of the sensor cable are accommodated in a tubular carrier casing which is correspondingly circular shape in section. In the sectional area of the sensor cable, the two pairs of FBG strands are located on X- and Y-axes which intersect perpendicularly with each other at the center of the sensor cable. In this case, one pair of FBG strands are located on X-axis while the other pair are located on Y-axis. However, the provision of the perpendicularly intersecting X- and Y-axes is not necessarily an imperative requisite. In this connection, it is desirable that the refractive index change portions in each one of the FBG strands be located in the same or substantially the same position in the sectional area of the sensor cable. However, if desired, one pair of FBG may be located in a deviated position relative to the other pair of FBG.

The refractive index change portions which are formed periodically in a predetermined pitch in each one of the FBG strands of the sensor cable may have the same index of refraction. Otherwise, refractive index change portions with different indices of refraction may be arranged in the axial direction of the sensor cable. However, the refractive index change portions which are located in the same coordinate position in the sectional area of the sensor cable should have the same index of refraction. A variation in index of refraction relative to the core portion of the fiber results in a corresponding variation in Bragg wavelength.

In case different refractive index change portion are provided in FBG, reflected light from each refractive index change portion contains information with regard to the degree of bending and the position of FBG. Further, the bending direction of the FBG sensor cable can be detected from reference signals in various Bragg wavelengths and the amounts of shift from respective wavelengths. Accordingly, on the basis of the reflection diffraction light signal from the respective refractive index change portions of FBG, it is possible to detect in what direction and to what extent the sensor cable is bent. For this purpose, the light beam to be input to FBG from a light source should contain respective Bragg wavelengths. Namely, the light source should be arranged to project a composite light beam of the respective wavelength or to sweep the respective wavelengths one after another.

In a case where FBG is provided with a plural number of refractive index change portions all having the same index of refraction, it becomes necessary to detect the positions of the respective refractive index change portions. To this end, for example, the positions of the respective refractive index change portions can be detected by the use of an interferometer. More specifically, for this purpose, one may use an interferometer using an incident light from a light source as reference light and matching the length of light path of the reference light with that of reflection diffraction light from each one of the refractive index change portions for measurement of interference. Therefore, in this case, it is desirable to employ a light source which is arranged to project a low coherence light beam, for measuring interference one after another for each one of the refractive index change portions.

The FBG sensor cable is applicable to an elongated flexible body which has an internal coextensive axial passage to place the sensor cable in. In use, the elongated flexible body is inserted into an internal cavity and invisible from outside like a flexible insertion tube of an endoscope. More specifically, in case the sensor cable is to be placed in an endoscopic biopsy channel for detection of three-dimensional shapes of a flexible insertion tube of an endoscope, it is desirable for the sensor cable to have an outside diameter close to the inside diameter of the biopsy channel, as long as placement of the sensor cable is not hindered by tightness.

DESCRIPTION OF PREFERRED EMBODIMENTS

Figure 1:
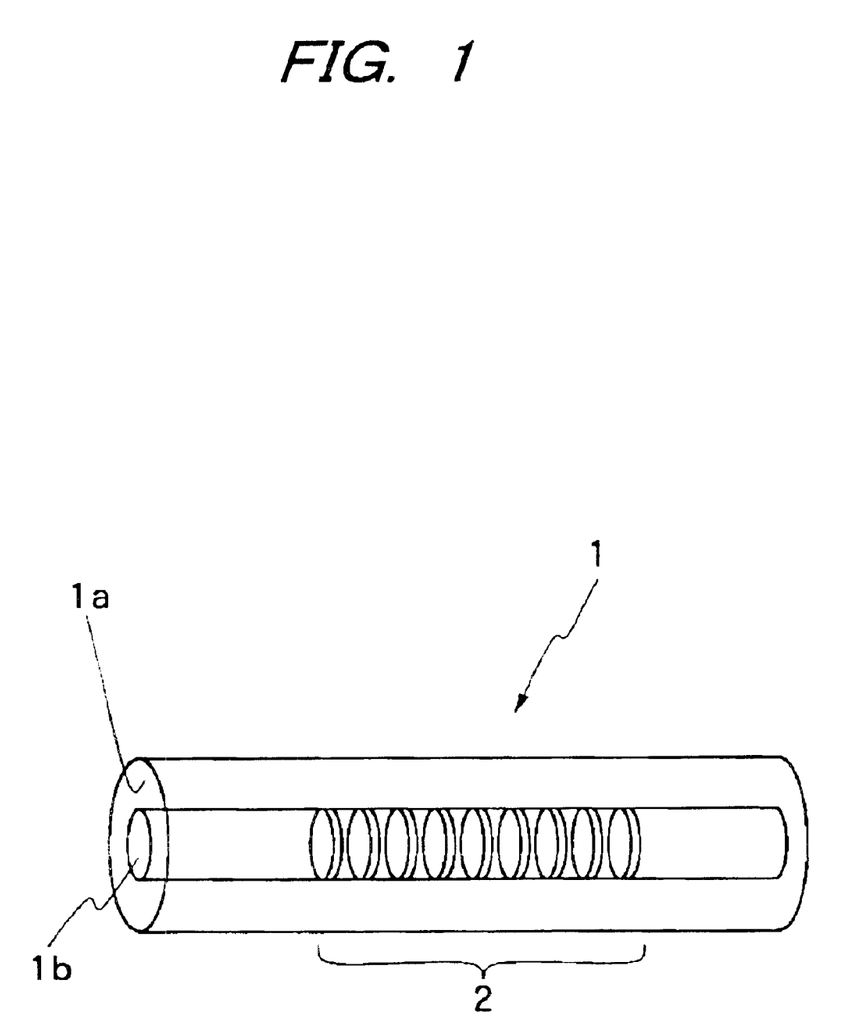
FIG. 1 is a schematic illustration explanatory of the construction of refractive index change portions of a fiber Bragg grating (FBG) strand employed in the present invention.

Hereafter, the present invention is described more particularly by way of its preferred embodiments with reference to the accompanying drawings. Referring first to FIG. 1, there is schematically shown the construction of a FBG strand. In FIG. 1, indicated at 1*a* is a cladding portion and at 1*b* is a core portion of a FBG strand 1. The FBG strand 1 is formed by inserting the core portion 1*b* in the cladding portion 1*a*. The FBG strand 1 is provided with refractive index change portions 2 in its core portion 1*b*, where the index of refraction is varied. At the refractive index change portions 2, the index of refraction is changed periodically over a predetermined length which corresponds to an ultimate sensor length. When light of Bragg wavelengths is incident on this FBG strand, reflection diffraction light signals are obtained from the reflective index change portions 2. As the fiber is bent from a straight reference state, the refractive index portions 2 are strained and as a result the length of the sensor is varied. Elongation of the sensor length causes the reflection diffraction light a shift to a longer wavelength from a wavelength in the reference state. When the sensor length is shortened, it causes the reflection diffraction light a shift to a shorter wavelength. The amount of the shift in wavelength which occurs to the reflection diffraction light varies depending upon the degree of the straining of the refractive index change portions 2.

Figure 2:
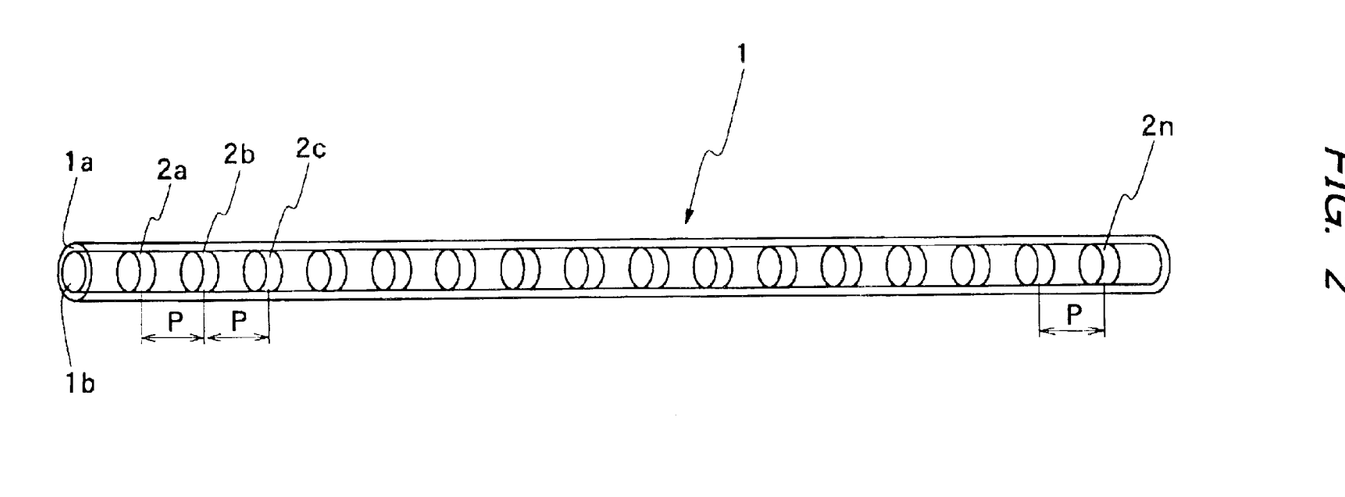
FIG. 2 is a schematic illustration explanatory of the construction of the fiber Bragg grating strand as a whole.
Figure 3:
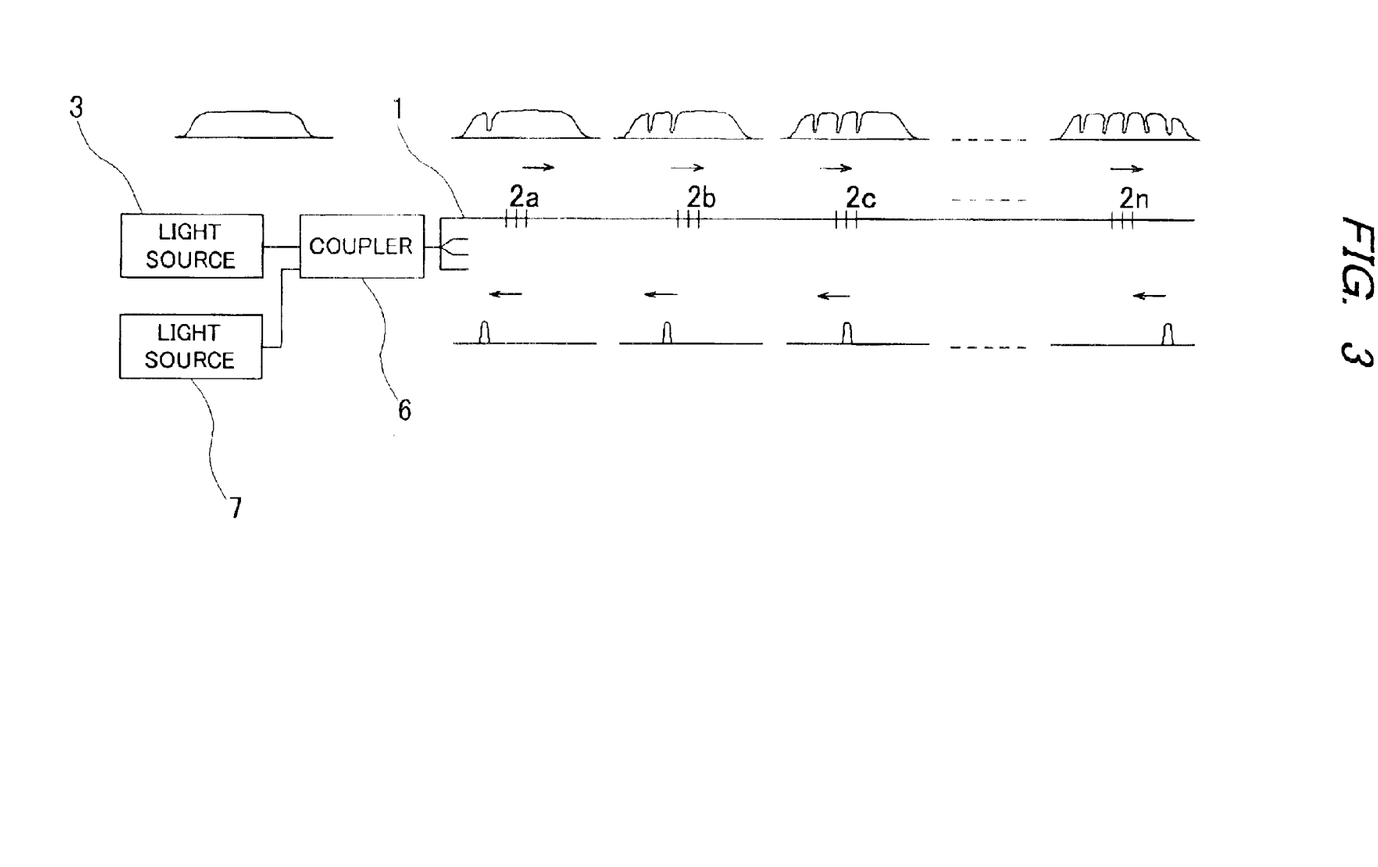
FIG. 3 is a schematic illustration showing the manner of obtaining reflection diffraction light signals from refractive index change portions of a fiber Bragg grating strand in a first embodiment of the present invention.

In this connection, as shown in FIG. 2, a plural number of refractive index change portions 2a, 2b, 2c . . . 2n are provided periodically in a predetermined pitch P. In a case where these refractive index change portions 2a, 2b, 2c, . . . 2n are arranged to have different refractive indices from each other, the reflection diffraction light is obtained from the respective varied refractive index sections at different Bragg wavelengths λ1, λ2, λ3 . . . λn as shown in FIG. 3. Accordingly, in case a light signal which contains the wavelength ranges λ1 to λn is fed into four FBG strands 1 from a light source 3, reflection diffraction light components of wavelengths λ1, λ2, λ3, . . . λn are obtained from the refractive index change portions 2a, 2b, 2c, . . . 2n, respectively. These reflection diffraction light components contain signals indicative of positions of bends in the longitudinal direction of the FBG strands 1 along with direction and degree of the bending.

Figure 4:
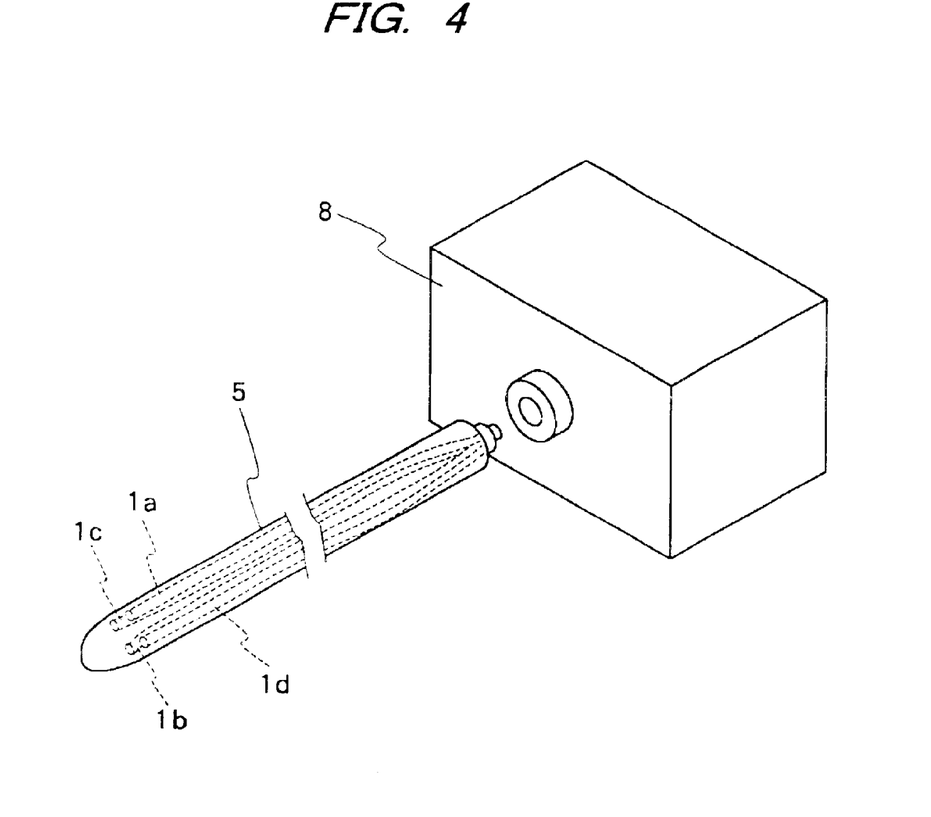
FIG. 4 is a schematic illustration of a sensor cable and a control unit.
Figure 5:
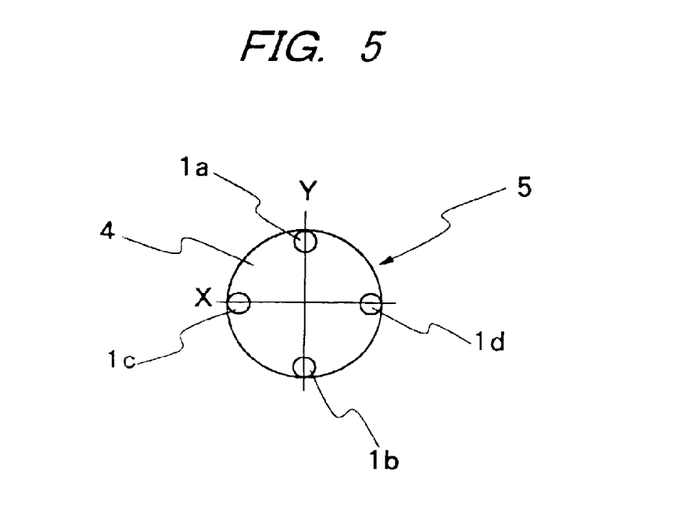
FIG. 5 is a diagrammatic illustration explanatory of the construction of the sensor cable.

As shown in FIGS. 4 and 5, four FBG strands 1, with the properties as described above, are located on or in positions in the proximity of the circumference of a round flexible columnar or cylindrical carrier casing 4 of rubber or soft synthetic resin material at intervals of 90 degrees from each other. In this case, as shown in FIG. 5, there is obtained a sensor cable 5 having two pairs of FBG strands on two perpendicularly intersecting axes X and Y, namely, a first pair of FBG strands 1a and FBG 1b (a fiber couple on Y-axis) and a second pair of FBG strands 1c and 1d (a fiber couple on X-axis) with angular intervals of 180 degrees from each other. In the axial direction of the sensor cable 5, refractive index change portions 2a, 2b, 2c, . . . 2n of the respective FBG strands 1a to 1d are located on the same sectional planes. The sensor cable 5 is disconnectibly connectible to a control unit 8 with a light source 3, coupler 6 and signal processor 7 built in its housing.

Within the housing of the control unit 8, signal light from the light source 3 is divided by a coupler 6 and fed to the respective FBG strands 1a to 1d, and reflection diffraction light signals from the respective varied refractive index sections are fed to the signal processor 7 and thereby processed through predetermined signal processing operations. As a consequence, when the sensor cable 5 is bent at some point, it is possible to detect at what position, in what direction and to what extent the sensor cable 5 is bent, that is to say, it becomes possible to recognize the three-dimensional shape of the sensor cable. If desired, a light circulator may be used in place of the coupler 6.

Figure 6:
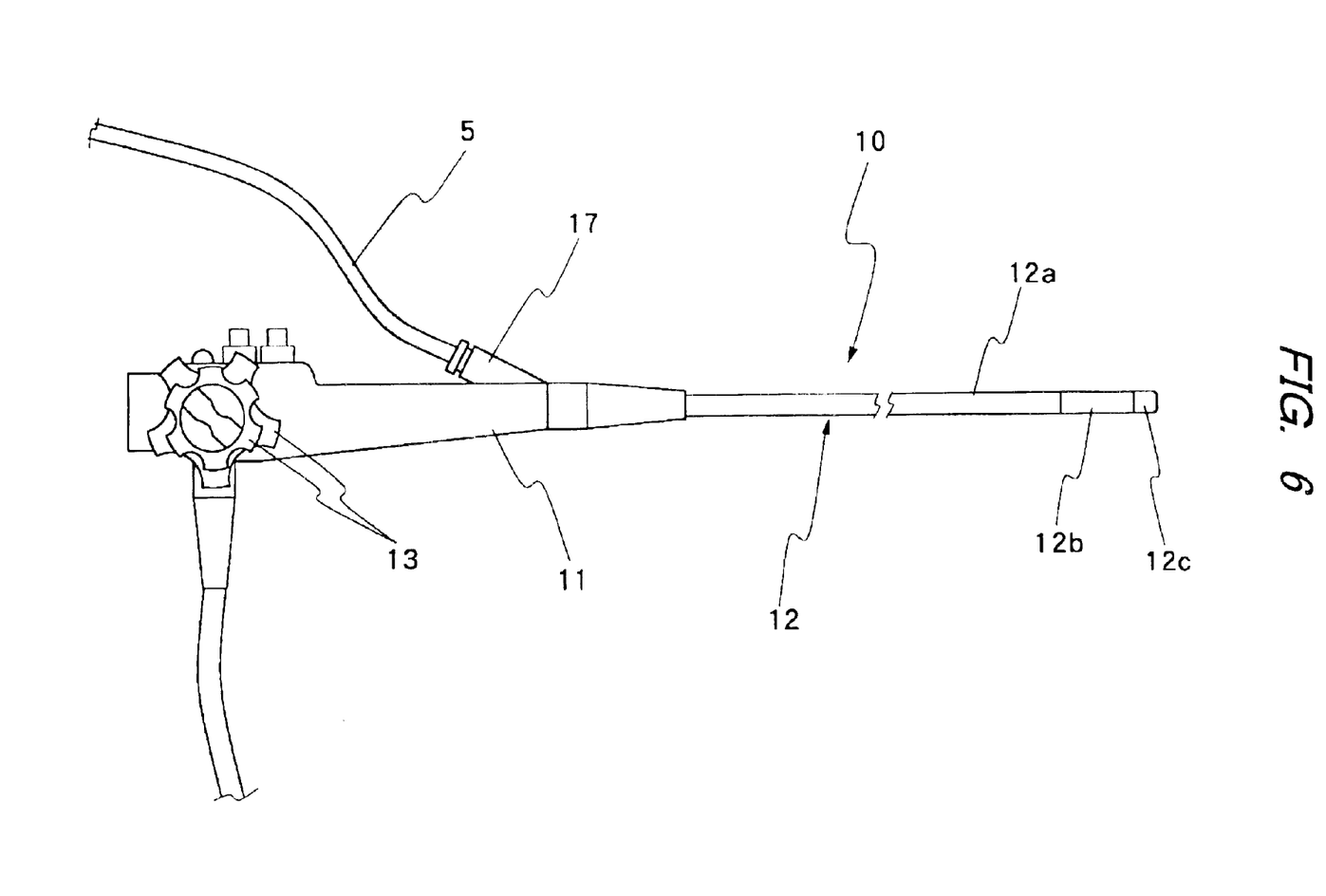
FIG. 6 is a schematic illustration showing the general layout of an endoscope with an elongated flexible insertion tube, a typical example to which the sensor cable is applicable for detection of three-dimensional shapes.
Figure 7:
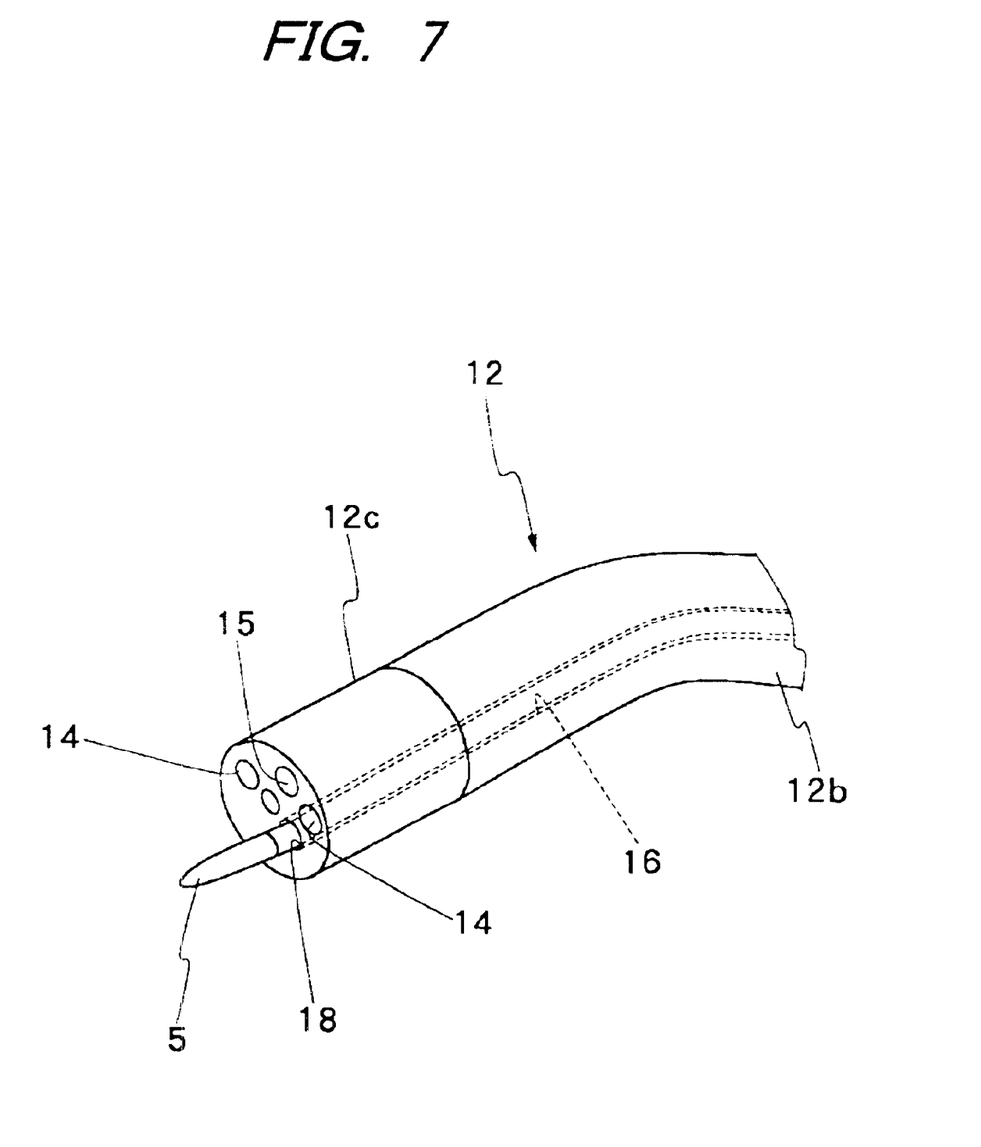
FIG. 7 is a schematic illustration showing a sensor cable which has been inserted into a biopsy channel in the endoscopic insertion tube.

In use, the above-described sensor cable 5 is placed in a passage or channel within an elongated flexible member to detect three-dimensional shapes of the elongated flexible member. As for example of the elongated flexible member, an elongated flexible insertion tube 12 of an endoscope 10 is shown in FIGS. 6 and 7. The flexible insertion tube 12 is extended out from and connected to a manipulating head assembly 11 of the endoscope 10. A major part of the insertion tube 12 consists of a flexible body section 12a which can be bent in arbitrary bending directions at the time of the insertion tube is introduced into a body cavity through a bent path of insertion. An angle section 12b and a rigid tip end section 12c are successively connected to the fore end of the flexible body section 12a. The angle section 12b can be angularly bent by remote control to turn the rigid tip end section into a desired direction. For operating the angle section 12b, an angulation knob 13 is mounted on the manipulating head assembly 11 as an angulation control means.

As well known in the art, an endoscopic observation mechanism, including illumination windows 14 and an endoscopic observation window 15, is mounted on the rigid tip end section 12c of the insertion tube 12. More particularly, an entrance way 17 to a biopsy channel is provided in the vicinity of the proximal end of the insertion tube 12 which is connected to the manipulating head assembly 11. On the other hand, an exit way 18 of the biopsy channel is opened in a casing of the rigid tip end section 12c in the vicinity of the above-mentioned endoscopic observation mechanism. The biopsy channel 16 is constituted by a flexible tube with sufficient flexibility in bending directions, and extended through the endoscopic insertion tube 12 in such a way as to connect the entrance way 17 with the exit way 18. The sensor cable 5 is placed in the biopsy channel 16 for detection of three-dimensional shapes of the endoscopic insertion tube 12 within a body cavity. In this connection, in order to detect three-dimensional shapes of the insertion tube 12 accurately, it is desirable to minimize the diametric differential between the outside diameter of the sensor cable 5 and the inside diameter of the endoscopic biopsy channel 16 within a range which would not hinder insertion of the sensor cable 5.

In the foregoing description, the flexible insertion tube 12 of the endoscope 10 is shown as an object in measuring three-dimensional shapes of an elongated flexible member according to the method of the present invention. Above all, it is important to detect three-dimensional shapes of a flexible insertion tube of a colonoscope which is usually required to inch the insertion tube toward a target intracavitary site of interest through a path of insertion containing bends of complicate shapes which can easily be turned into different shapes by application of external forces. The recognition of three-dimensional shapes is extremely advantageous from the standpoint of enabling smooth and quick insertion of the endoscope to an intracavitary site of interest while lessening pains on the part of the patient.

Figure 8:
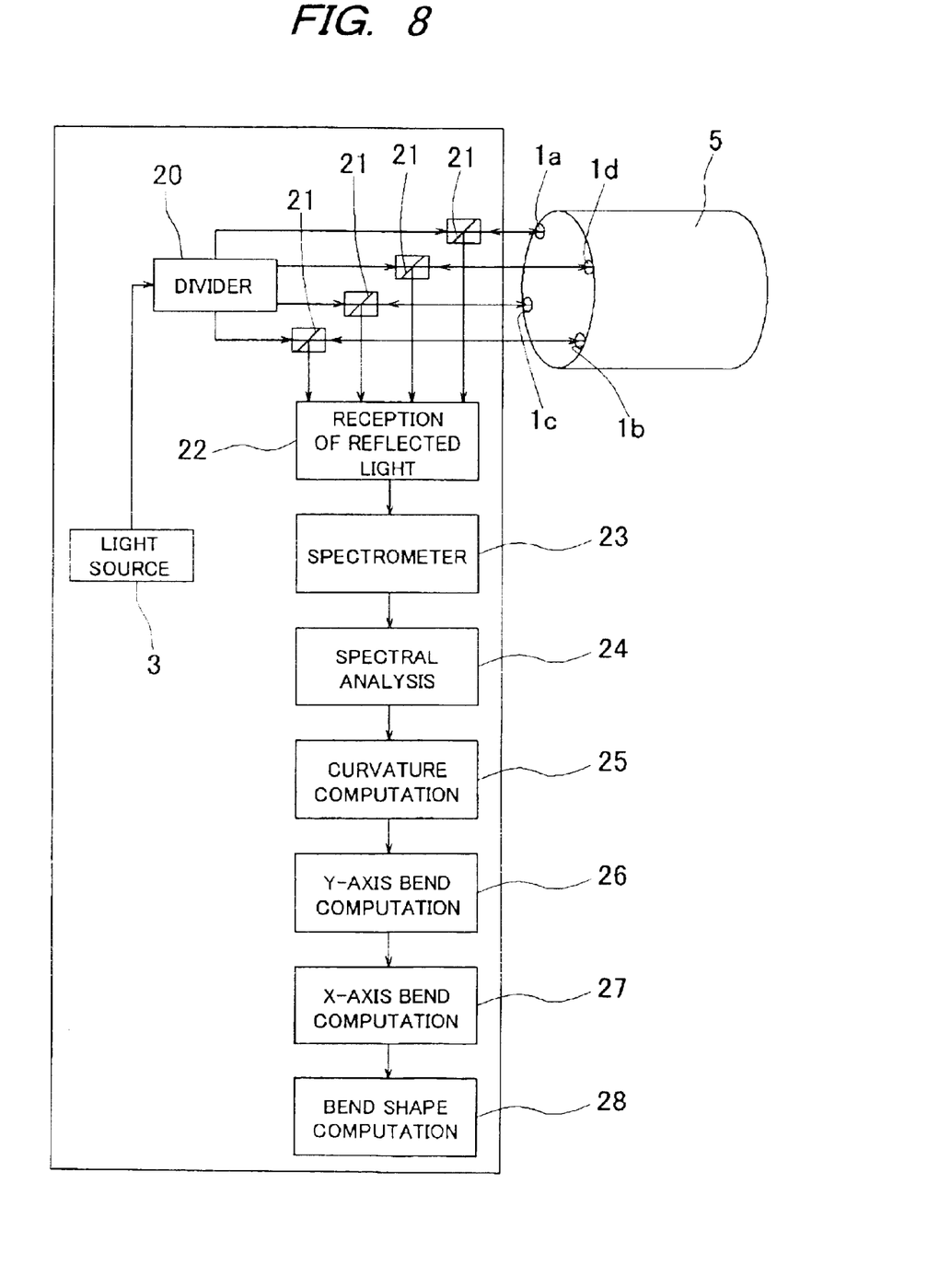
FIG. 8 is a diagrammatic illustration of a mechanism for detecting 3D shapes of the sensor cable.

The signal light beam which is projected from the light source 3 contains wavelength bands λ1 to λn. As shown in FIG. 8, the signal light is divided into four light fluxes at the source light flux divider 20 and the respective light fluxes are passed through a beam splitter 21 and separately fed to light input ends of the FBG strands 1a to 1d. As a result, reflection diffraction light signals of wavelengths λ1, λ2, λ3, . . . λn come out from the refractive index change sections 2a, 2b, 2c, . . . 2n within the respective FBG strands 1a to 1d. These returned reflection diffraction light signals are reflected off the beam splitters 21 and shed on the reflection light receiver 22. At the reflection light receiver, reflection diffraction light signals from refractive index change sections 2a to 2n in each one of the FBG strands 1a to 1d are sequentially taken in, for example, by the use of a switching means.

Figure 9:
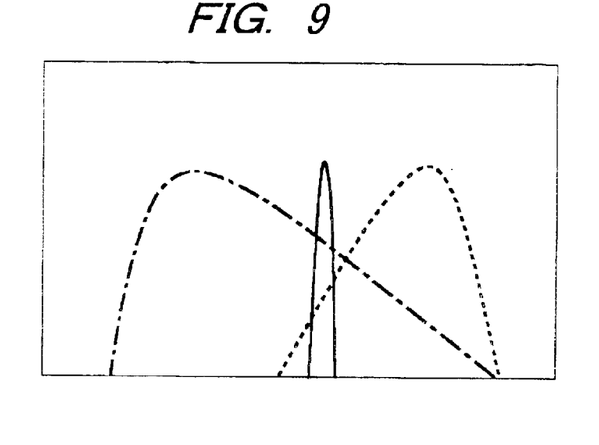
FIG. 9 is a diagram showing waveforms of reflection diffraction light from reflective index change portions.

The thus obtained signals of reflection diffraction light from the FBG strands 1a to 1d are each checked for spectral distribution by spectroscopic analysis. In this regard, shown by solid line in FIG. 9 is the spectrum of reflection diffraction light from a reference refractive index change section which is free of distortions or strains by bending. Indicated by one-dot chain line in the same figure is the spectrum of reflection diffraction light from a refractive index change section which is in a bent state. Therefore, a peak value of each reflection diffraction signal is detected at a spectrum analyzer 24 to determine a difference from a reference wavelength, that is to say, to determine the amount of shift of each reflection diffraction signal. If there is no shift in the wavelength of the reflection diffraction light, in other words, if it is substantially same as the wavelength of a reference reflection diffraction light signal, the FBG strands 1a to 1d are considered in a rectilinear state. If there is a shift in wavelength, the sensor cable 5 is considered to be in a bent state. For example, in a case where there are positive (+) shifts in wavelengths of return signals from the FBG strands 1a and 1c and negative (−) shifts in wavelengths of return signals from the FBG strands 1b and 1d, it is considered that the refractive index change sections of the FBG strands 1a and 1c which are on the outer side of a bend are elongated while the refractive index change sections of FBG strands 1b and 1d which are on the inner side of a bend are shrunk. Besides, the radius of curvature varies correspondingly in relation with the amount of shift in wavelength. Namely, greater the amount of shift in wavelength, the smaller becomes the radius of curvature of a bend.

Figure 10:
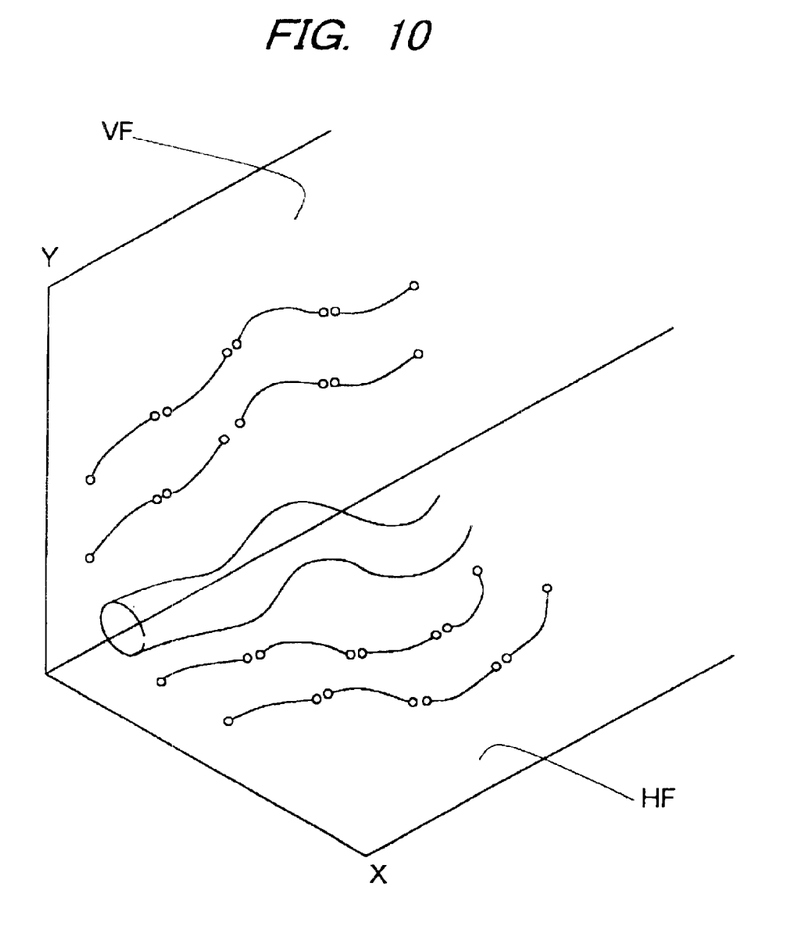
FIG. 10 is a diagram of loci of fiber Bragg gratings plotted on a 3D coordinate system to build up a three-dimensional shape of the sensor cable.

Now, in the case of the sensor cable 5, a three-dimensional coordinate system is formed as shown in FIG. 10, having X-, Y- and Z-axes represented by the FBG strands 1c and 1d, FBG strands 1a and 1b and the axial direction of the sensor cable 5, respectively. For displaying three-dimensional shapes of the sensor cable 5, values in direction and extent of bending of the sensor cable 5 are plotted on this three-dimensional coordinate system.

For this purpose, firstly amounts of shifts from a reference wavelength, which occurred to the refractive index change sections 2a to 2n of the FBG strands 1a and 1b, are computed at a radius of curvature computation circuitry 25 to determine radii of curvature of the refractive index change sections 2a to 2n. Further, radii of curavture of the refractive index change sections 2a to 2n of the FBG strands 1c and 1d are determined in a similar manner. In this instance, the interval between preceding and succeeding refractive index change sections in the sensor cable is P.

On the basis of the results of arithmetic operations by the radius of curvature computation circuitry 25, loci of the FBG strands 1a and 1b in the direction of Z-axis and on a plane VF containing Y-axis are determined at a Y-axis flexure computation circuitry 26 from the radii of curvature of the refractive index change sections of the FBG strands 1a and 1b and the interval P between the preceding and succeeding refractive index change sections. Further, in a similar manner, loci of FBG strands 1c and 1d in the direction of z-axis and on a plane HF containing x-axis are determined from the radii of curvature of the refractive index change sections of the FBG strans 1c and 1d and the interval P between the preceding and succeeding refractive index change sections.

Then, the data from the y-axis flexure computation circuitry 26 and the X-axis flexure computation circuitry 27 are processed into graphical data of a three-dimensional shape of the sensor cable 5 at a 3D image processor circuitry 28. The obtained graphical data are of a three-dimensional shape of the sensor cable. However, since the sensor cable 5 is placed in a biopsy channel of the flexible insertion tube 12 of the endoscope 10, the three-dimensional shape of the sensor cable 5 can be deemed and displayed as a three-dimensional shape of the insertion tube 12.

Figure 11:
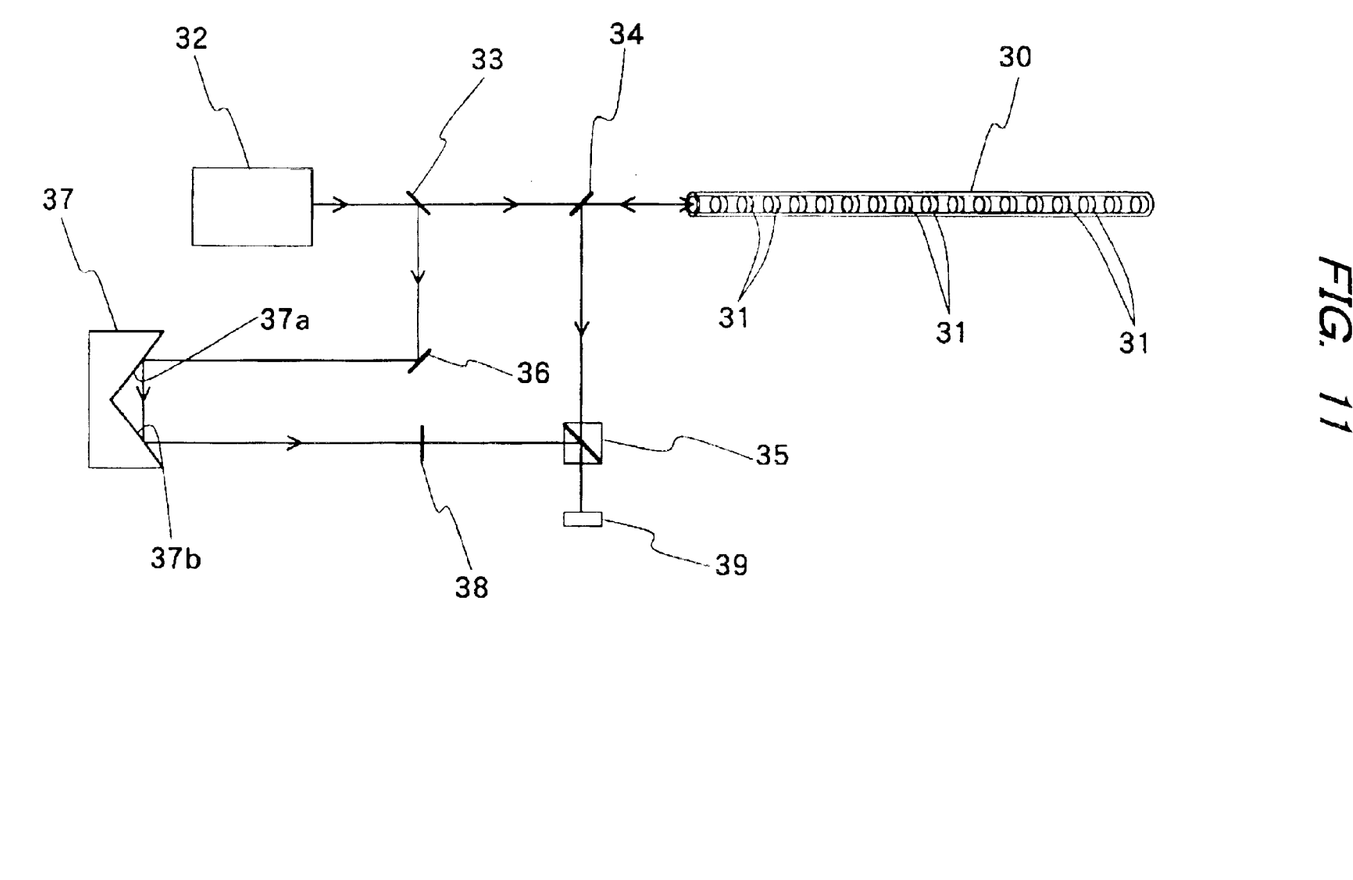
FIG. 11 is a diagrammatic illustration of a mechanism of detecting three-dimensional shapes of the sensor cable according to a second embodiment of the present invention.

Turning now to FIG. 11, there is shown a second embodiment of the present invention. In the case of this embodiment, all of the refractive index change sections 31 in a FBG strand 30 have the same refractive index. Accordingly, Bragg wavelength light, substantially consisting of a single wavelength, is projected from a light source 32. The light from the light source 32 is divided into a signal light beam to be fed to the FBG strand 30 and a reference light beam. The signal light is fed to the FBG 30 through a beam splitter 34 which is located in the path of the signal light. As a result, return signals of reflection diffraction light are obtained from the respective refractive index change portions 31. These return signals of reflection diffraction light are reflected off the beam splitter 34 and projected on a wave surface synthesizing beam splitter 35.

On the other hand, the reference light beam, which has been divided by the half mirror 33, is reflected off a reflecting mirror 36 to turn its light path and fed to a variable length light path means 37 and then to the wave surface synthesizing beam splitter 35 after converting its direction of polarization through a half wave plate 38. In this instance, the variable length light path means 37 is provided with reflecting surfaces 37a and 37b which are disposed at the angle of 90 degrees relative to each other, and can be moved in the direction of the arrow by a drive means which is not shown. Therefore, the length of the reference light path can be equalized with the length of light path of the reflection diffraction light from the respective refractive index change portions 31. Instead of the above-described arrangement, the variable length light path means can be arranged by the use of a retroreflector or a right-angle type prism.

Thus, by the variable length light path means 37, the length of the reference light path is sequentially adjusted to match the lengths of reflection diffraction light paths from the respective refractive index change portions 31 of the FBG strand 30. At the wave surface synthesizing beam splitter (or an optical circulator) 35, the reflection diffraction light from the FBG 31 is transmitted and the reference light is reflected off. In synthesizing the two wave surfaces, interference occur therebetween. Images of interference fringes are taken by a camera 39 to detect the extent of bending flexure at each one of the refractive index change portions 31 on the basis of the information of interference fringes. Namely, the greater the extent of flexure, the smaller becomes the interference fringe signal. Accordingly, three-dimensional shapes of an elongated flexible member like the endoscopic insertion tube 12 can be measured by the use of a sensor cable with four FBG strands in a manner similar to the above-described first embodiment of the invention. Besides, the degree of bending flexure at each refractive index change portion 31 can be detected on the basis of interference fringe information. Accordingly, in this case, there is no necessity for processing reflection diffraction light signals from four FBG strands for spectral analysis.

What is claimed is:

1. A device for detecting three-dimensional shapes of an elongated flexible body, comprising:
    a sensor cable adapted to be inserted into an axial coextensive passage within an elongated flexible body, said sensor cable having two pairs of fiber Bragg grating strands each having a plural number of refractive index change portions periodically in a predetermined pitch;
    a light source connectible to each one of said fiber Bragg grating strands to input a light beam containing a Bragg wavelength to said refractive index change portions; and
    a signal processor adapted to receive reflection diffraction light signals from said refractive index change portions of each fiber Bragg grating strand, and to detect a three-dimensional shape of said elongated flexible body by measuring degree of straining at each one of said refractive index change portions by way of comparison of said reflection diffraction light signals with a reference wavelength.

2. A device for detecting three-dimensional shapes as defined in claim 1, wherein said pairs of fiber Bragg grating strands are accommodated in a round tubular carrier casing and located on two perpendicularly intersecting axes and at positions on or close to inner periphery of said round tubular casing.

3. A device for detecting three-dimensional shapes as defined in claim 2, wherein said refractive index change portions in each one of said fiber Bragg grating strands are formed substantially at same positions in axial direction.

4. A device for detecting three-dimensional shapes as defined in claim 2, wherein said sensor cable is adapted to be placed in a biopsy channel extending through an insertion tube of an endoscope.

5. A device for detecting three-dimensional shapes as defined in claim 1, wherein said light source is arranged to emit a signal light in a predetermined wavelength band, and said refractive index change portions in each one of said fiber Bragg grating strands are adapted to generate reflection diffraction light signals with respect to different Bragg wavelengths, and said signal processor is adapted to detect strains in said refractive index change portions on the basis of a shift of each reflection diffraction light signal from a reference wavelength.

6. A device for detecting three-dimensional shapes as defined in claim 1, wherein said light source is of a low coherence light beam, said refractive index change portions in each one of said fiber Bragg grating strands are adapted to generate reflection diffraction light signals with respect to the same Bragg wavelength, and said signal processor further includes an interferometer to check for interference between reflection diffraction light signal from each one of said refractive index change portions and reference light, detecting strains in said refractive index change portions on the basis of intensity of interference light.

* * * * *